US011344311B2

(12) United States Patent
Gerberding (10) Patent No.: US 11,344,311 B2
(45) Date of Patent: *May 31, 2022

(54) ANEURYSM DEVICES WITH ADDITIONAL ANCHORING MECHANISMS AND ASSOCIATED SYSTEMS AND METHODS

(71) Applicant: PULSAR VASCULAR, INC., Los Gatos, CA (US)

(72) Inventor: Brent Gerberding, San Jose, CA (US)

(73) Assignee: PULSAR VASCULAR, INC., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/827,286

(22) Filed: Mar. 23, 2020

(65) Prior Publication Data

US 2020/0214713 A1    Jul. 9, 2020

Related U.S. Application Data

(63) Continuation of application No. 14/130,738, filed as application No. PCT/US2012/040558 on Jun. 1, 2012, now Pat. No. 10,624,647.
(Continued)

(51) Int. Cl.
*A61B 17/12* (2006.01)
*A61F 2/82* (2013.01)

(52) U.S. Cl.
CPC .... *A61B 17/12113* (2013.01); *A61B 17/1214* (2013.01); *A61B 17/12118* (2013.01); *A61B 17/12172* (2013.01); *A61F 2002/823* (2013.01)

(58) Field of Classification Search
CPC ........ A61B 17/12113; A61B 17/12118; A61B 17/1214; A61B 17/12172;
(Continued)

(56) References Cited

U.S. PATENT DOCUMENTS 3,868,956 A    3/1975    Alfidi et al.
4,164,045 A    8/1979    Bokros et al.
(Continued)

FOREIGN PATENT DOCUMENTS

AU    2006304660 A1    4/2007
CN    1298287 A    6/2001
(Continued)

OTHER PUBLICATIONS

Chinese Office Action issued in corresponding Chinese Application No. 201310106823.8.
(Continued)

*Primary Examiner* — Kelly J Bekker
*Assistant Examiner* — Paige A Codrington
(74) *Attorney, Agent, or Firm* — Troutman Pepper Hamilton Sanders LLP (57) ABSTRACT

The present technology relates to aneurysm devices with additional anchoring mechanisms, and associated systems and methods. The aneurysm device is endovascularly deliverable to a site proximate an aneurysm near a parent artery with bifurcating branches. The device can include a closure structure comprising a distal-facing aspect configured to at least partially occlude the aneurysm. The closure structure can be formed from a generally flat pattern and is transformable between a compressed configuration and a deployed configuration. The device can also have one or more lodging elements which fold to form loop elements configured for anchoring within at least one of the bifurcating branches. The struts of the lodging elements can include hinge points which bias the folding of the lodging elements. The devices further include a supplemental stabilizer connected to the closure structure and configured to reside in the parent artery.

17 Claims, 2 Drawing Sheets

Related U.S. Application Data (60) Provisional application No. 61/493,356, filed on Jun. 3, 2011.

(58) Field of Classification Search
CPC ........ A61B 17/12131; A61B 17/12168; A61B 21/12022; A61B 2017/00867; A61F 2/954; A61F 2/0095; A61F 2/0013; A61F 2/0063; A61F 2002/823; A61F 2002/016
USPC ........................................................ 606/200
See application file for complete search history.

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,554,181 A | 9/1996 | Das |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| 5,855,597 A | 1/1999 | Jayaraman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A | 3/2000 | Abrams et al. |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,391,037 B1 | 5/2002 | Greenhalgh |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,592,605 B2 | 7/2003 | Lenker et al. |
| 6,613,074 B1 | 9/2003 | Mitelberg et al. |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |
| 6,863,678 B2 | 3/2005 | Lee et al. |

(56) References Cited

U.S. PATENT DOCUMENTS

| | | | |
|---|---|---|---|
| 6,890,218 B2 | 5/2005 | Patwardhan et al. |
| 6,911,037 B2 | 6/2005 | Gainer et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,306,622 B2 | 12/2007 | Jones et al. |
| 7,322,960 B2 | 1/2008 | Yamamoto et al. |
| 7,343,856 B2 | 3/2008 | Blohdorn |
| 7,387,629 B2 | 6/2008 | Vanney et al. |
| 7,410,482 B2 | 8/2008 | Murphy et al. |
| 7,503,928 B2 * | 3/2009 | Case .............. A61F 2/2475 623/1.24 |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,247 B2 | 2/2011 | Conston |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Porter |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 * | 11/2015 | Losordo .......... A61B 17/12036 |
| 9,192,388 B2 | 11/2015 | Cam et al. |
| 9,211,124 B2 | 12/2015 | Campbell et al. |
| 9,232,992 B2 | 1/2016 | Heidner |
| 9,259,229 B2 | 2/2016 | Abrams et al. |
| 9,277,924 B2 * | 3/2016 | Clarke ............ A61B 17/12022 |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,831 B2 | 4/2017 | Gerberding et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,117 B2 | 5/2017 | Bachman |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,510 B2 | 6/2018 | Gerberding |
| 2002/0026232 A1 | 2/2002 | Marotta et al. |
| 2002/0107534 A1 | 8/2002 | Schaefer et al. |
| 2003/0009177 A1 | 1/2003 | Middleman et al. |
| 2003/0033003 A1 | 2/2003 | Harrison et al. |
| 2003/0057156 A1 | 3/2003 | Peterson et al. |
| 2003/0139802 A1 | 7/2003 | Wulfman et al. |
| 2003/0144695 A1 | 7/2003 | McGuckin, Jr. et al. |
| 2003/0158595 A1 | 8/2003 | Randall |
| 2003/0171730 A1 | 9/2003 | Kelly et al. |
| 2003/0171739 A1 | 9/2003 | Murphy |
| 2003/0181922 A1 | 9/2003 | Alferness |
| 2003/0181942 A1 | 9/2003 | Sutton et al. |
| 2003/0195385 A1 | 10/2003 | DeVore |
| 2003/0195553 A1 | 10/2003 | Wallace et al. |
| 2003/0199923 A1 | 10/2003 | Khairkhahan |
| 2003/0212412 A1 | 11/2003 | Dillard et al. |
| 2004/0019324 A1 | 1/2004 | Duchamp |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0143254 A1 | 7/2004 | Vanney et al. |
| 2004/0158185 A1 | 8/2004 | Moran et al. |
| 2004/0158311 A1 | 8/2004 | Berhow et al. |
| 2004/0167567 A1 | 8/2004 | Cano et al. |
| 2004/0167597 A1 | 8/2004 | Constantino et al. |
| 2004/0167602 A1 | 8/2004 | Fischell et al. |
| 2004/0172056 A1 | 9/2004 | Guterman et al. |
| 2004/0186491 A1 | 9/2004 | Klint et al. |
| 2004/0193206 A1 | 9/2004 | Gerberding et al. |
| 2004/0193246 A1 | 9/2004 | Ferrera |
| 2004/0193253 A1 | 9/2004 | Thorpe et al. |
| 2004/0210248 A1 | 10/2004 | Gordon et al. |
| 2004/0210298 A1 | 10/2004 | Rabkin et al. |
| 2004/0260241 A1 | 12/2004 | Yamamoto et al. |
| 2005/0021023 A1 | 1/2005 | Guglielmi et al. |
| 2005/0025797 A1 | 2/2005 | Wang et al. |
| 2005/0033349 A1 | 2/2005 | Jones et al. |
| 2005/0033409 A1 | 2/2005 | Burke et al. |

(56) References Cited

U.S. PATENT DOCUMENTS

| | | |
|---|---|---|
| 2005/0055049 A1 | 3/2005 | McGuckin, Jr. et al. |
| 2005/0096728 A1 | 5/2005 | Ramer |
| 2005/0177224 A1 | 8/2005 | Fogarty et al. |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |
| 2006/0200234 A1 | 9/2006 | Hines |
| 2006/0206199 A1 | 9/2006 | Churchwell et al. |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1* | 8/2007 | Eskridge .......... A61B 17/12022 606/213 |
| 2007/0198075 A1 | 8/2007 | Levy |
| 2007/0203567 A1 | 8/2007 | Levy |
| 2007/0239251 A1 | 10/2007 | Bose |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0097586 A1 | 4/2008 | Pavcnik et al. |
| 2008/0103582 A1 | 5/2008 | Randall |
| 2008/0147100 A1 | 6/2008 | Wallace |
| 2008/0183143 A1 | 7/2008 | Palisis et al. |
| 2008/0221600 A1 | 9/2008 | Dieck et al. |
| 2008/0269774 A1 | 10/2008 | Garcia et al. |
| 2008/0281350 A1 | 11/2008 | Sepetka |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0299403 A1 | 12/2009 | Chanduszko |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1* | 4/2010 | Gerberding ...... A61B 17/12113 606/213 |
| 2010/0324649 A1 | 12/2010 | Mattsson |
| 2011/0022149 A1 | 1/2011 | Cox et al. |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0283768 A1 | 11/2012 | Cox et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1* | 8/2013 | Clarke ............. A61B 17/12145 606/198 |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0058420 A1 | 2/2014 | Hannes et al. |
| 2014/0121752 A1 | 5/2014 | Losordo et al. |
| 2014/0128901 A1 | 5/2014 | Kang et al. |
| 2014/0135812 A1 | 5/2014 | Divino et al. |
| 2014/0142608 A1 | 5/2014 | Eskridge et al. |
| 2014/0180377 A1 | 6/2014 | Bose et al. |
| 2014/0200607 A1 | 7/2014 | Sepetka et al. |
| 2014/0236216 A1 | 8/2014 | Gerberding |
| 2015/0039015 A1 | 2/2015 | Gerberding |
| 2015/0142025 A1 | 5/2015 | Brandeis |
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0216687 A1 | 8/2015 | Gerberding et al. |
| 2015/0245932 A1 | 9/2015 | Molaei et al. |
| 2015/0250628 A1 | 9/2015 | Monstadt et al. |
| 2015/0282962 A1 | 10/2015 | Strauss et al. |
| 2015/0327867 A1 | 11/2015 | Bachman et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0036153 A1 | 2/2016 | Beaman et al. |
| 2016/0038153 A1 | 2/2016 | Losordo et al. |
| 2016/0249936 A1 | 9/2016 | Clarke et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |

(56) References Cited

U.S. PATENT DOCUMENTS

| | | | |
|---|---|---|---|
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| CN | 1384726 | 12/2002 |
| CN | 1399530 A | 2/2003 |
| CN | 1399531 A | 2/2003 |
| CN | 101489492 A | 7/2009 |
| CN | 102202585 A | 9/2011 |
| CN | 102762156 A | 10/2012 |
| CN | 103230290 A | 8/2013 |
| CN | 103381101 A | 11/2013 |
| CN | 103582460 A1 | 2/2014 |
| CN | 103607964 A | 2/2014 |
| DE | 102008028308 A1 | 4/2009 |
| EP | 0820726 A2 | 1/1998 |
| EP | 00996372 A1 | 5/2000 |
| EP | 1269935 A2 | 1/2003 |
| EP | 1527753 A2 | 5/2005 |
| EP | 1951129 A2 | 8/2008 |
| EP | 2326259 A1 | 6/2011 |
| EP | 2451363 A2 | 5/2012 |
| EP | 2713905 A1 | 4/2014 |
| HK | 1134421 A1 | 3/2014 |
| JP | 2001286478 A | 10/2001 |
| JP | 2002516705 A | 6/2002 |
| JP | 2003512129 A | 4/2003 |
| JP | 2005522266 A | 7/2005 |
| JP | 2009512515 A | 3/2009 |
| JP | 2013226419 A | 11/2013 |
| KR | 20080081899 A | 9/2008 |
| WO | WO-9724978 A1 | 7/1997 |
| WO | WO-9726939 A1 | 7/1997 |
| WO | WO-9731672 A1 | 9/1997 |
| WO | WO-9823227 A1 | 6/1998 |
| WO | WO-9850102 A1 | 11/1998 |
| WO | 1999/002094 A1 | 1/1999 |
| WO | WO-9905977 A1 | 2/1999 |
| WO | WO-9907294 A1 | 2/1999 |
| WO | WO-9915225 A1 | 4/1999 |
| WO | WO-0013593 A1 | 3/2000 |
| WO | WO-0130266 A1 | 5/2001 |
| WO | WO-2001093782 | 12/2001 |
| WO | 02/00139 A1 | 1/2002 |
| WO | WO-0213899 A1 | 2/2002 |
| WO | WO-02071977 | 9/2002 |
| WO | WO-02078777 | 10/2002 |
| WO | WO-02087690 | 11/2002 |
| WO | WO-03059176 A2 | 7/2003 |
| WO | WO-03075793 A1 | 9/2003 |
| WO | WO-04019790 A1 | 3/2004 |
| WO | WO-04026149 A1 | 4/2004 |
| WO | WO-04105599 A1 | 12/2004 |
| WO | WO-05033409 A1 | 4/2005 |
| WO | WO-05082279 A1 | 9/2005 |
| WO | WO-2006119422 A2 | 11/2006 |
| WO | WO-2007/047851 A2 | 4/2007 |
| WO | WO-2008/151204 A1 | 12/2008 |
| WO | WO-2010/028314 A1 | 3/2010 |
| WO | WO-2011029063 A2 | 3/2011 |
| WO | 2012/167156 A1 | 12/2012 |
| WO | WO-2012167137 A1 | 12/2012 |
| WO | WO-2012167150 A1 | 12/2012 |
| WO | WO-2013052920 A1 | 4/2013 |
| WO | WO-2013169380 A1 | 11/2013 |
| WO | WO-2014029835 A1 | 2/2014 |
| WO | WO-2015179377 A1 | 11/2015 |

OTHER PUBLICATIONS https://www.thefreedictionary.com/hinge, definition of the term "hinge", retrieved Aug. 18, 2019 (Year: 2019).
Cordis NeuroVascular, Inc.; "Masstransit Microcatheter," Product Prochure; No. 153-8383-3; Miami Lakes, FL, USA (2003).
Cordis NeuroVascular, Inc.; "Prolwer Select Plus Microcatheter," Product Brochure; No. 154-9877-1; Miami Lakes, FL, USA (2003).
Cordis NeuroVascular, Inc.; "Prowler Select LP Microcatheter," Product Brochure; No. 155-5585; Miami Lakes, FL, USA (2004).
Cordis NeuroVascular, Inc.; "Rapid Transit Microcatheter," Product Brochure; No. 152-7369-2; Miami Lakes, FL, USA (2003).
Extended European Search Report, European Application No. 06826291.4, dated Nov. 19, 2009, 7 pages.
Gupta et al. SMST-2003: Proc. Intl. Conf. Shape Memory Superelastic Technol.; Pacific Grove, CA; p. 639; 2003.
International Search Report and Written Opinion for Application No. PCT/US2010/047908, dated May 25, 2011, 11 pages.
International Search Report and Written Opinion for International Application No. PCT/US2009/056133, dated Oct. 26, 2009, 11 pages.
International Search Report and Written Opinion for International Application No. PCT/US2010/047908, dated Mar. 15, 2012, 11 pages.
International Search Report and Written Opinion for International Application No. PCT/US2012/040552, dated Aug. 28, 2012, 14 pages.
International Search Report and Written Opinion for International Application PCT/US2012/040536, dated Oct. 15, 2012, 17 pages.
International Search Report and Written Opinion for International Application PCT/US2012/040558, dated Oct. 8, 2012, 17 pages.
International Search Report and Written Opinion for International Application PCT/US2012/059133, dated Mar. 11, 2013, 15 pages.
International Search Report and Written Opinion for International Application PCT/US2013/031793, dated Jun. 26, 2013, 14 pages.
International Search Report for International Application No. PCT/US06/40907, dated May 1, 2008, 2 pages.
Micrus Copr.; "Concourse 14 Microcatheter" Product Brochure; Sunnyvale ,CA, USA.
Polytetraflouroethylene Implants, DermNet NZ, Nov. 11, 2005, http://dermetnz.org/polytetrafluoroethylene.html.
Singapore Examination Report for Singapore Application No. 200802811-0, dated Jul. 12, 2009, 7 pages.

\* cited by examiner

ANEURYSM DEVICES WITH ADDITIONAL ANCHORING MECHANISMS AND ASSOCIATED SYSTEMS AND METHODS

CROSS-REFERENCE TO RELATED APPLICATIONS

The present application is a continuation of pending U.S. patent application Ser. No. 14/130,738, filed on Oct. 2, 2014, which is a U.S. National Phase Application under 35 U.S.C. § 371 of International Patent Application No. PCT/US12/40558, filed Jun. 1, 2012 which claims the benefit of priority of U.S. Provisional Patent Application No. 61/493,356, filed on Jun. 3, 2011, each of which is incorporated herein by reference in its entirety.

TECHNICAL FIELD

The present technology relates to implantable therapeutic devices at a target site, such as an opening at a neck of an aneurysm. In particular, the present technology is generally directed to aneurysm devices with additional anchoring mechanisms and associated systems and methods.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. The risks related to anesthesia, bleeding, and infection associated with these types of procedures are high, and tissue that is affected during the procedure may or may not survive and continue functioning.

Minimally invasive techniques for treating aneurysms are accordingly highly desirable. In general, the minimally invasive therapeutic objective is to prevent material that collects or forms in the aneurysm cavity from entering the bloodstream and to prevent blood from entering and collecting in the aneurysm. This is often accomplished by introducing various materials and devices into the aneurysm. For example, implantable vaso-occlusive metallic structures are well known and commonly used. Many conventional vaso-occlusive devices have helical coils constructed from a shape memory material or noble metal that forms a desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

It is crucial to accurately implant such vaso-occlusive devices within the internal volume of a cavity and to maintain the device within the internal volume of the aneurysm. Migration or projection of a vaso-occlusive device from the cavity may interfere with blood flow or nearby physiological structures and poses a serious health risk. In addition to the difficulties of delivering implantable occlusion devices, some types of aneurysms are challenging to treat because of structural features of the aneurysm or because of particularities of the site. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms. It is therefore challenging to position conventional implantable devices during deployment, prevent shifting or migration of such devices after deployment, and preserve blood flow in neighboring vessels following after deployment.

DETAILED DESCRIPTION

The present disclosure describes implantable therapeutic devices and methods for endovascular placement of devices at a target site, such as an opening at a neck of an aneurysm. In particular, selected embodiments of the present technology are directed to devices having additional anchoring mechanisms for lodging at bifurcated branches at the neck of the aneurysm. The following description provides many specific details for a thorough understanding of, and enabling description for, embodiments of the disclosure. Well-known structures, systems, and methods often associated with aneurysm treatment systems have not been shown or described in detail to avoid unnecessarily obscuring the description of the various embodiments of the disclosure. In addition, those of ordinary skill in the relevant art will understand that additional embodiments may be practiced without several of the details described below.

Figure 1:
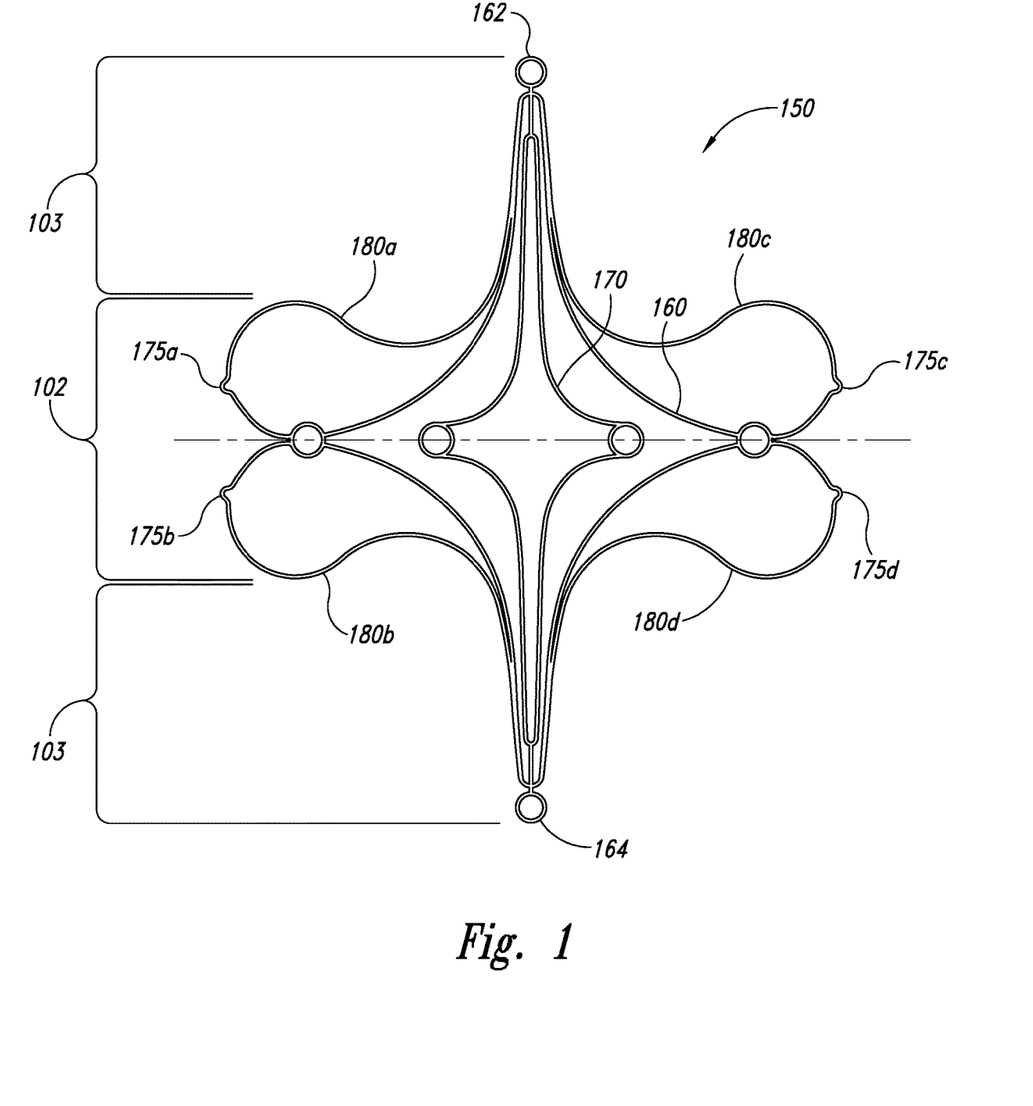
FIG. 1 is a top plan view of an aneurysm device configured in accordance with an embodiment of the technology.
Figure 2:
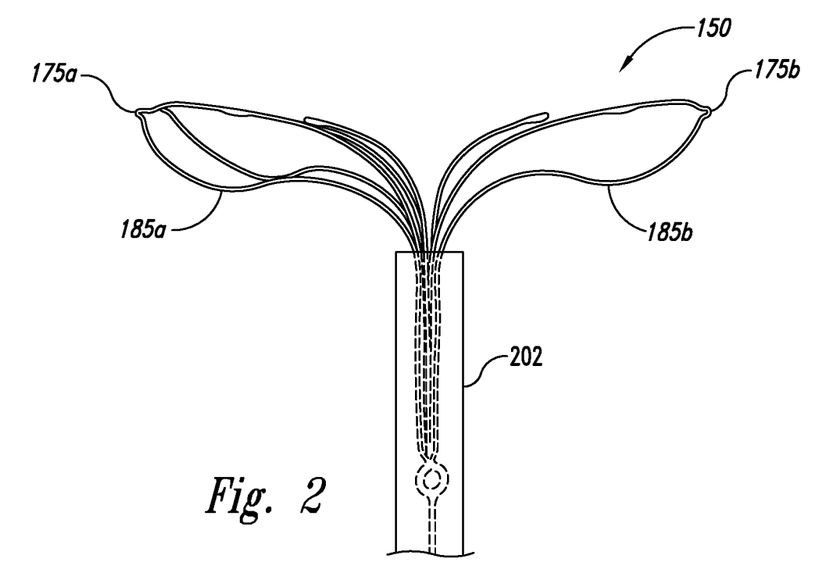
FIG. 2 is a side view of the aneurysm device of FIG. 1 in a partially deployed configuration.

FIGS. 1 and 2 illustrate an embodiment of an aneurysm device 150 configured in accordance with the present technology. In particular, FIG. 1 is a top plan view of the aneurysm device 150 in a substantially flat, pre-assembled configuration, and FIG. 2 is a side view of the aneurysm device 150 in a deployed configuration. Referring to FIG. 1, the aneurysm device 150 can comprise a closure structure 102 and a supplemental stabilizer or support 103 extending from the closure structure 102. The closure structure 102 can be a frame, scaffold, or other structure that at least partially occludes the neck of an aneurysm to prevent embolic coils or other coagulative material within the aneurysm from escaping into the bloodstream. The closure structure 102 includes a perimeter support 160 and an inner support 170. The perimeter support 160 and inner support 170 can be joined at junctions 162 and 164. The supplemental stabilizer 103 is shown in an unassembled stage in FIG. 1. Once assembled, the proximally extending sides of the closure structure 102 and the supplemental stabilizer 103 hold the curved portion of the closure structure 102 at the neck of the aneurysm.

The aneurysm device 150 can have struts 180*a-d* projecting proximally from the junctions 162 and 164. Struts 180*a* and 180*c* can be connected at junction 162 and struts 180*b* and 180*d* are connected at junction 164 to form the supplemental stabilizer 103 with proximal anchoring segments. In one embodiment, the struts 180*a-d* each include a hinge point or bend point 175a-d. The hinge points 175a-d define collapse points and allow the struts 180a-d to preferentially fold down in a manner that forms additional supporting elements for the aneurysm device 150 that can be lodged in side artery branches at an aneurysm neck.

In the embodiment illustrated in FIG. 1, the aneurysm device 150 is constructed from a substantially flat substrate by cutting, etching, stamping, or otherwise forming the framework of the closure structure 102, the unassembled supplemental stabilizer 103, and the hinge points 175a-d. The closure structure 102 and the supplemental stabilizer 103 can be constructed from a flat sheet of material having substantially uniform thickness, but in other embodiments different regions of the sheeted material can have different thicknesses corresponding to the desired thickness for portions of the closure structure 102 and/or the supplemental stabilizer 103. Further, in other embodiments the aneurysm device 150 may be formed using different techniques and/or materials.

FIG. 2 is a side view of the aneurysm device 150 in a partially deployed configuration. In particular, as the aneurysm device 150 is deployed from a delivery catheter 202, loop elements 185a and 185b form and begin to fully open. The loop elements 185a-b start to open as the delivery catheter 202 is being withdrawn and fully open when the delivery catheter 202 is fully withdrawn. As described in greater detail below with reference to FIG. 3, the loop elements 185a-b are configured to provide a mechanism for the aneurysm device 150 to anchor in bifurcated side branches when deployed across the neck of an aneurysm. In other embodiments, the loop elements 185a-b can have a different arrangement and/or the aneurysm device 150 may include a different number of loop elements 185.

Figure 3:
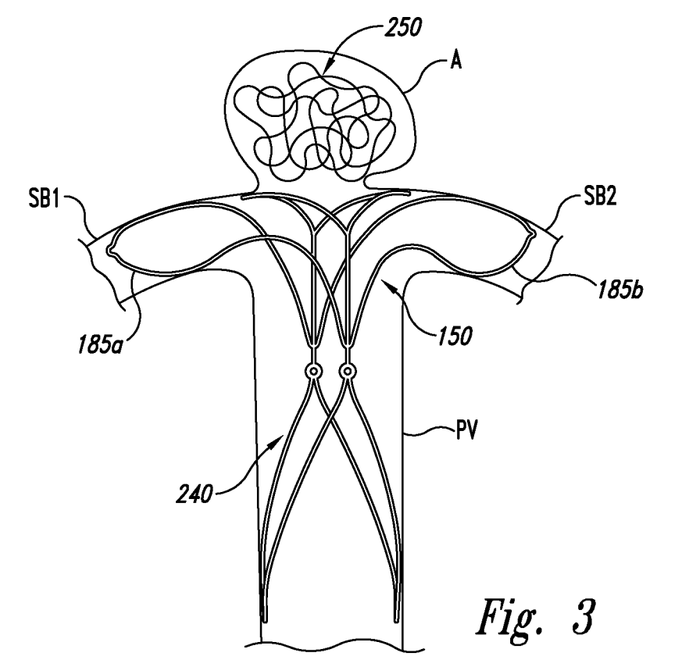
FIG. 3 is a view of the aneurysm device of FIGS. 1 and 2 deployed at the neck of an aneurysm and lodged at the bifurcated side artery branches.

FIG. 3 illustrates the aneurysm device 150 of FIGS. 1 and 2 deployed at the neck of an aneurysm A with anchoring legs 240. As mentioned above, when the aneurysm device 150 is deployed, the loop elements 185a-b open and can lodge in side branch vessels SB 1 and SB 2, respectively. The lodging of the loop elements 185a-b within the side branch vessels SB 1 and SB 2 is expected to provide additional anchoring mechanisms for the aneurysm device 150 at the aneurysm A, and is expected to provide more secured lodging/deployment of the aneurysm device 150.

FIG. 3 additionally illustrates the use of the aneurysm device 150 to retain debris and/or other materials, such as an embolic coil mass 250, within the aneurysm cavity. In one embodiment, for example, implantable devices of the present technology may be deployed to retain debris and/or previously placed materials within the aneurysm cavity. In another embodiment, implantable devices of the present technology may be deployed before placing materials, such as embolic materials, coils, and the like, in the aneurismal cavity, and then the materials may be placed through the openings in the closure structure. In this situation, the aneurysm device may be retracted following placement of the embolic materials, or it may be detached and left at the site.

EXAMPLES

1. An aneurysm device endovascularly deliverable to a site proximate an artery with bifurcating branches, the aneurysm device comprising:
   a closure structure comprising a distal-facing aspect configured to at least partially block an opening to the aneurysm and a proximal-facing aspect configured to arch over lumina of the bifurcating branches; and
   a supplemental stabilizer connected to the closure structure, the supplemental stabilizer configured to reside in the artery;
   wherein the closure structure includes a hinge point at which the closure structure folds to form a loop element configured for anchoring within at least one of the bifurcating branches.

2. The aneurysm device of example 1 wherein the closure structure comprises struts.

3. The aneurysm device of example 2 wherein the hinge point is formed on one of the struts.

4. The aneurysm device of example 1 wherein the closure structure comprises four hinge points.

5. The aneurysm device of example 1 wherein the closure structure is transformable between a compressed configuration and a deployed configuration.

6. The aneurysm device of example 5, further comprising a catheter configured to retain the closure structure in the compressed configuration.

7. The aneurysm device of example 1 wherein the closure structure comprises two loop elements, each individual loop element configured to lodge in one of the bifurcating branches.

8. The aneurysm device of example 1 wherein the closure structure comprises a shape memory material.

9. A system for treating an aneurysm, the system comprising:
   a distal framework portion comprising a distal-facing aspect configured to enclose the aneurysm, wherein the distal framework includes a plurality of struts, and wherein individual struts include a hinge point; and
   a proximal support framework connected to the distal framework portion, the support framework configured to reside in the parent artery and biased to press outward against a luminal wall thereof.

10. The system of example 9, further comprising a delivery sheath configured to temporarily retain the distal framework in a compressed configuration.

11. The system of example 9 wherein the struts comprise a generally flexible material that preferentially bends at the hinge point.

12. The system of example 9 wherein the individual struts comprise a loop shape that bends at the hinge point.

13. The system of example 9 wherein the distal framework portion is formed from a generally flat, unassembled component into a three-dimensional, assembled component.

14. A method of treating an aneurysm located at a site proximate to a parent artery that bifurcates into downstream branches, the method comprising:
   expanding an axially-compressed framework comprising a distal portion and a proximal portion at a site proximate to the aneurysm, wherein the distal portion comprises a plurality of struts having bend points; and
   arching the distal portion of the framework unobtrusively over lumina of the downstream branches, wherein the struts comprise loops bent at the bend points, the loops configured to lodge in the downstream branches.

15. The method of example 14, further comprising forming the framework from a substantially flat material.

16. The method of example 14, further comprising delivering the framework to the site with a catheter, wherein delivering the framework comprises temporarily restraining the framework in a generally compressed configuration.

17. The method of example 14, further comprising extracting the framework from the parent artery.

18. The method of example 17 wherein extracting the framework comprises restraining the framework in a catheter in a generally compressed configuration.

19. The method of example 14, further comprising substantially enclosing the aneurysm with the distal portion of the framework.

20. The method of example 14, further comprising detaching the framework from a delivery device.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. In particular, the clot removal devices described above with reference to particular embodiments can include one or more additional features or components, or one or more of the features described above can be omitted.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, B all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An aneurysm device endovascularly deliverable to a site proximate a parent artery with bifurcating branches, the aneurysm device comprising:
   a closure structure comprising a central occlusion element configured to at least partially block an opening to an aneurysm at the site;
   a supplemental stabilizer connected to the closure structure and configured to arch over lumina of the bifurcating branches; and
   one or more lodging elements comprising struts, the struts including hinge points formed by apices extending outwardly from the struts and pointing generally toward an axis defined by a centerline of the closure structure;
   wherein the one or more lodging elements fold at the hinge points to form loop elements configured for extending into one of the bifurcating branches from the central occlusion element; and
   wherein the hinge points are offset from the centerline of the closure structure.

2. The aneurysm device of claim 1, wherein the lodging elements comprise a pair of hinge points disposed on opposing sides of a respective loop element.

3. The aneurysm device of claim 1, wherein the closure structure comprises a plurality of struts.

4. The aneurysm device of claim 3, wherein the struts of the closure structure form a perimeter support and an inner support.

5. An aneurysm device endovascularly deliverable to a site proximate a parent artery with bifurcating branches, the aneurysm device comprising:
   a closure structure comprising a central occlusion element configured to at least partially block an opening to an aneurysm at the site;
   a supplemental stabilizer connected to the closure structure and configured to arch over lumina of the bifurcating branches; and
   one or more lodging elements comprising struts, the struts including hinge points formed by apices extending outwardly from the struts and pointing generally toward an axis defined by a centerline of the closure structure;
   wherein the one or more lodging elements fold at the hinge points to form loop elements configured for extending into one of the bifurcating branches from the central occlusion element;
   wherein the closure structure comprises a plurality of struts;
   wherein the struts of the closure structure form a perimeter support and an inner support; and
   wherein the perimeter support and the inner support connect at one or more junctions offset from the centerline of the closure structure.

6. The aneurysm device of claim 1, wherein the closure structure is transformable between a compressed configuration and a deployed configuration.

7. The aneurysm device of claim 1, wherein the closure structure comprises a shape memory material.

8. A system for treating an aneurysm at a site proximate a parent artery with bifurcating branches, the system comprising:
   a distal framework portion comprising a distal-facing aspect configured to enclose the aneurysm and one or more lodging elements configured to extend into the bifurcating branches in opposing directions from the distal-facing aspect, the lodging elements having a plurality of struts; and
   a proximal support framework connected to the distal framework portion and configured to press outward against a luminal wall of the parent artery;
   wherein the struts of the lodging elements include a hinge point at apices outwardly extending from the struts, the apices pointing generally toward an axis defined by a centerline of the distal framework portion;
   wherein the one or more lodging elements fold at the hinge point to form loop elements configured for anchoring within at least one of the bifurcating branches; and
   wherein the struts of the one or more lodging elements of the distal framework portion form a perimeter support and an inner support, the perimeter support and the inner support connecting at one or more junctions offset from the centerline of the distal framework portion.

9. A system for treating an aneurysm at a site proximate a parent artery with bifurcating branches, the system comprising:
  a distal framework portion comprising a distal-facing aspect configured to enclose the aneurysm and one or more lodging elements configured to extend into the bifurcating branches in opposing directions from the distal-facing aspect, the one or more lodging elements having a plurality of struts; and
  a proximal support framework connected to the distal framework portion and configured to press outward against a luminal wall of the parent artery;
  wherein the struts of the lodging elements include a hinge point at apices outwardly extending from the struts, the apices pointing generally toward an axis defined by a centerline of the distal framework portion;
  wherein the one or more lodging elements fold at the hinge point to form loop elements configured for anchoring within at least one of the bifurcating branches; and
  wherein the hinge point of the lodging elements is offset from the centerline of the distal framework portion.

10. The system of claim 8, wherein the struts of the lodging elements comprise a loop shape that bends at the hinge point.

11. The system of claim 8, wherein the distal framework portion is formed from a generally flat, unassembled component into a three-dimensional, assembled component.

12. A method of treating an aneurysm located at a site proximate to a parent artery that bifurcates into downstream branches, the method comprising:
  expanding an axially-compressed framework comprising a distal portion and a proximal portion at a site proximate to the aneurysm, wherein the distal portion comprises a plurality of struts, the struts comprising loops bent at bend points offset from a centerline of the distal portion, the loops configured to lodge in the downstream branches;
  wherein the bend points are formed by apices outwardly extending from a curve in the struts, the apices pointing generally toward an axis defined by the centerline of the distal portion.

13. The method of claim 12, further comprising:
  forming the framework from a substantially flat material.

14. The method of claim 12, further comprising:
  delivering the framework to the site with a catheter, wherein delivering the framework comprises temporarily restraining the framework in a generally compressed configuration.

15. The method of claim 12, further comprising:
  extracting the framework from the site proximate the aneurysm.

16. The method of claim 15, wherein the step of extracting the framework comprises restraining the framework in a catheter in a generally compressed configuration.

17. The method of claim 12, further comprising:
  detaching the framework from a delivery device.

* * * * *